US008382711B2

United States Patent
Dudar et al.

(10) Patent No.: US 8,382,711 B2
(45) Date of Patent: Feb. 26, 2013

(54) INTRAVENOUS PUMPING AIR MANAGEMENT SYSTEMS AND METHODS

(75) Inventors: Thomas Dudar, Palatine, IL (US); Ross Krogh, Long Grove, IL (US); James Martucci, Libertyville, IL (US); Shmuel Sternberg, Palatine, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/981,152

(22) Filed: Dec. 29, 2010

(65) Prior Publication Data

US 2012/0172800 A1    Jul. 5, 2012

(51) Int. Cl.
*A61M 1/00* (2006.01)

(52) U.S. Cl. .......................................... 604/123

(58) Field of Classification Search .................. 604/122, 604/123
See application file for complete search history.

(56) References Cited

U.S. PATENT DOCUMENTS

| | | |
|---|---|---|
| 250,868 A | 12/1881 | Abbott |
| 927,476 A | 7/1909 | Barker |
| 1,505,050 A | 8/1924 | Lauritsen |
| 2,292,007 A | 8/1942 | Morgan |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,342,019 A | 9/1967 | Smythe |
| 3,390,677 A | 7/1968 | Razimbaud |
| 3,412,760 A | 11/1968 | Franck |
| 3,527,572 A | 9/1970 | Urkiewicz |
| 3,581,464 A | 6/1971 | Bhuta et al. |

(Continued)

FOREIGN PATENT DOCUMENTS

| | | |
|---|---|---|
| DE | 1806654 | 5/1970 |
| EP | 0058325 | 8/1982 |

(Continued)

OTHER PUBLICATIONS

PCT Search Report Application No. US2008/068078 dated Mar. 24, 2009, Baxter International Inc.

(Continued)

*Primary Examiner* — Nicholas Lucchesi
*Assistant Examiner* — Aarti B Berdichevsky
(74) *Attorney, Agent, or Firm* — K&L Gates LLP

(57) ABSTRACT

An intravenous ("IV") liquid delivery system includes: an IV pump tubing set; a shuttle pump or membrane pump actuator operable with the IV pump tubing set; upstream and downstream valve actuators operable with the IV pump tubing set; the IV pump tubing set including an air removal device; an air detector configured to sense air in the IV pump tubing set; a control unit configured and arranged to (i) open the upstream valve actuator and close the downstream valve actuator to allow the pump actuator to draw liquid into a pump actuation portion of the IV pump tubing set, and (ii) close the upstream valve actuator and open the downstream valve actuator to allow the pump actuator to push liquid out of the pump actuation portion, the system configured to attempt to remove the air via the air removal device while operating the upstream and downstream valve actuators according to (i) and (ii).

16 Claims, 7 Drawing Sheets

U.S. PATENT DOCUMENTS

| | | | |
|---|---|---|---|
| 3,598,727 | A | 8/1971 | Wilock |
| 3,631,654 | A | 1/1972 | Riely |
| 3,650,093 | A | 3/1972 | Rosenberg |
| 3,677,710 | A | 7/1972 | Hirsch |
| 3,744,492 | A | 7/1973 | Leibinsohn |
| 3,769,207 | A | 10/1973 | Baer |
| 3,771,288 | A | 11/1973 | Wisman et al. |
| 3,795,088 | A | 3/1974 | Esmond |
| 3,827,561 | A | 8/1974 | Serfass et al. |
| 3,834,386 | A | 9/1974 | Sisley |
| 3,849,071 | A | 11/1974 | Kayser |
| 3,908,653 | A | 9/1975 | Kettering |
| 3,964,479 | A | 6/1976 | Boag et al. |
| 3,976,311 | A | 8/1976 | Spendlove |
| 3,985,134 | A | 10/1976 | Lissot et al. |
| 3,996,027 | A | 12/1976 | Schnell et al. |
| 4,013,072 | A | 3/1977 | Jess |
| 4,031,891 | A | 6/1977 | Jess |
| 4,031,894 | A | 6/1977 | Urquhart et al. |
| 4,038,190 | A | 7/1977 | Baudet et al. |
| 4,047,563 | A | 9/1977 | Kurata |
| 4,048,995 | A | 9/1977 | Mittleman |
| 4,054,522 | A | 10/1977 | Pinkerton |
| 4,060,485 | A | 11/1977 | Eaton |
| 4,061,031 | A | 12/1977 | Grimsrud |
| 4,102,655 | A | 7/1978 | Jeffery et al. |
| 4,137,160 | A | 1/1979 | Ebling et al. |
| 4,149,860 | A | 4/1979 | Kulik |
| 4,151,088 | A | 4/1979 | Wolf, Jr. et al. |
| 4,191,182 | A | 3/1980 | Popovich et al. |
| 4,200,095 | A | 4/1980 | Reti |
| 4,293,413 | A | 10/1981 | Schnell |
| 4,298,358 | A | 11/1981 | Ruschke |
| 4,304,670 | A | 12/1981 | Watanabe et al. |
| 4,311,137 | A | 1/1982 | Gerard |
| 4,325,715 | A | 4/1982 | Bowman et al. |
| 4,344,777 | A | 8/1982 | Siposs |
| 4,345,919 | A | 8/1982 | Wilkinson et al. |
| 4,345,999 | A | 8/1982 | Sigdell et al. |
| 4,353,368 | A | 10/1982 | Slovak et al. |
| 4,363,641 | A | 12/1982 | Finn, III |
| 4,368,118 | A | 1/1983 | Siposs |
| 4,427,009 | A | 1/1984 | Wells et al. |
| 4,433,971 | A | 2/1984 | Lindsay et al. |
| 4,486,188 | A | 12/1984 | Altshuler et al. |
| 4,493,705 | A | 1/1985 | Gordon et al. |
| 4,512,163 | A | 4/1985 | Wells et al. |
| 4,531,937 | A | 7/1985 | Yates |
| 4,568,333 | A | 2/1986 | Sawyer et al. |
| 4,583,981 | A | 4/1986 | Urquhart et al. |
| 4,586,925 | A | 5/1986 | Carlsson et al. |
| 4,622,032 | A | 11/1986 | Katsura et al. |
| 4,643,713 | A | 2/1987 | Viitala |
| 4,643,715 | A | 2/1987 | Isono et al. |
| 4,666,598 | A | 5/1987 | Heath et al. |
| 4,681,606 | A | 7/1987 | Swan, Jr. et al. |
| 4,715,398 | A | 12/1987 | Shouldice et al. |
| 4,722,725 | A | 2/1988 | Sawyer et al. |
| 4,722,731 | A | 2/1988 | Vailancourt |
| 4,734,269 | A | 3/1988 | Clarke et al. |
| 4,806,135 | A | 2/1989 | Siposs |
| 4,857,048 | A * | 8/1989 | Simons et al. ................ 604/503 |
| 4,932,987 | A | 6/1990 | Molina |
| 4,941,875 | A | 7/1990 | Brennan |
| 4,946,439 | A | 8/1990 | Eggers |
| D311,061 | S | 10/1990 | Vrana et al. |
| 4,976,685 | A | 12/1990 | Block, Jr. |
| 4,997,464 | A | 3/1991 | Kopf |
| 5,047,147 | A | 9/1991 | Chevallet et al. |
| 5,049,492 | A | 9/1991 | Sauer et al. |
| 5,059,173 | A | 10/1991 | Sacco |
| 5,061,236 | A | 10/1991 | Sutherland et al. |
| 5,061,365 | A | 10/1991 | Utterberg |
| 5,112,480 | A | 5/1992 | Hukasawa |
| 5,167,921 | A | 12/1992 | Gordon |
| 5,178,763 | A | 1/1993 | Delaunay |
| 5,204,000 | A | 4/1993 | Steadman et al. |
| 5,211,201 | A * | 5/1993 | Kamen et al. ..................... 137/1 |
| 5,228,889 | A | 7/1993 | Cortial et al. |
| 5,246,560 | A | 9/1993 | Nekoksa et al. |
| 5,268,077 | A | 12/1993 | Bubik et al. |
| 5,308,314 | A | 5/1994 | Fukui et al. |
| 5,328,461 | A | 7/1994 | Utterberg |
| 5,356,376 | A | 10/1994 | Milijasevic et al. |
| 5,358,481 | A | 10/1994 | Todd et al. |
| 5,368,555 | A | 11/1994 | Sussman et al. |
| 5,394,732 | A | 3/1995 | Johnson et al. |
| 5,411,705 | A | 5/1995 | Thor et al. |
| 5,421,815 | A | 6/1995 | Noguchi et al. |
| 5,429,595 | A | 7/1995 | Wright, Jr. et al. |
| 5,441,636 | A | 8/1995 | Chevallet et al. |
| 5,468,388 | A | 11/1995 | Goddard et al. |
| 5,489,385 | A | 2/1996 | Raabe et al. |
| 5,503,801 | A | 4/1996 | Brugger |
| 5,509,895 | A | 4/1996 | Noguchi et al. |
| 5,520,640 | A | 5/1996 | Utterberg |
| 5,578,070 | A | 11/1996 | Utterberg |
| 5,591,251 | A | 1/1997 | Brugger |
| 5,605,540 | A | 2/1997 | Utterberg |
| 5,637,081 | A | 6/1997 | Noguchi et al. |
| 5,643,205 | A | 7/1997 | Utterberg |
| 5,650,071 | A | 7/1997 | Brugger et al. |
| 5,674,199 | A | 10/1997 | Brugger |
| 5,681,294 | A | 10/1997 | Osborne et al. |
| 5,683,355 | A | 11/1997 | Fini et al. |
| 5,730,730 | A | 3/1998 | Darling, Jr. |
| 5,763,266 | A | 6/1998 | Palsson et al. |
| 5,776,091 | A | 7/1998 | Brugger et al. |
| 5,779,674 | A | 7/1998 | Ford |
| 5,800,597 | A | 9/1998 | Perrotta et al. |
| 5,830,185 | A | 11/1998 | Block, Jr. |
| 5,849,065 | A | 12/1998 | Wojke |
| 5,851,202 | A | 12/1998 | Carlsson |
| 5,858,239 | A | 1/1999 | Kenley et al. |
| 5,863,421 | A | 1/1999 | Peter, Jr. et al. |
| 5,895,368 | A | 4/1999 | Utterberg |
| 5,928,889 | A | 7/1999 | Bakich et al. |
| 5,931,990 | A | 8/1999 | Andrews |
| 5,951,870 | A | 9/1999 | Utterberg |
| 5,980,741 | A | 11/1999 | Schnell et al. |
| 5,983,947 | A | 11/1999 | Utterberg |
| 5,989,318 | A | 11/1999 | Schroll |
| 6,010,623 | A | 1/2000 | Schnell et al. |
| 6,019,824 | A | 2/2000 | Schnell |
| 6,046,806 | A | 4/2000 | Thompson |
| 6,051,134 | A | 4/2000 | Schnell et al. |
| 6,053,967 | A | 4/2000 | Heilmann et al. |
| 6,066,111 | A | 5/2000 | Brockhoff |
| 6,071,269 | A | 6/2000 | Schnell et al. |
| 6,099,512 | A | 8/2000 | Urrutia |
| 6,117,342 | A | 9/2000 | Schnell et al. |
| 6,171,484 | B1 | 1/2001 | Schnell et al. |
| 6,176,903 | B1 | 1/2001 | Wamsiedler |
| 6,187,198 | B1 | 2/2001 | Utterberg |
| 6,206,954 | B1 | 3/2001 | Schnell et al. |
| 6,251,167 | B1 | 6/2001 | Berson |
| 6,312,414 | B1 | 11/2001 | Brockhoff et al. |
| 6,344,139 | B1 | 2/2002 | Utterberg |
| 6,357,600 | B1 | 3/2002 | Scagliarini |
| 6,391,541 | B1 | 5/2002 | Petersen et al. |
| 6,391,638 | B1 | 5/2002 | Shaaltiel |
| 6,464,878 | B2 | 10/2002 | Utterberg |
| 6,481,455 | B2 | 11/2002 | Gustafson et al. |
| 6,514,255 | B1 | 2/2003 | Ferree |
| 6,537,356 | B1 | 3/2003 | Soriano |
| 6,562,107 | B2 | 5/2003 | Purdom et al. |
| 6,673,045 | B1 | 1/2004 | Kraus |
| 6,755,801 | B2 | 6/2004 | Utterberg et al. |
| 6,827,862 | B1 | 12/2004 | Brockhoff et al. |
| 7,722,577 | B2 | 5/2010 | Miner |
| 7,892,331 | B2 | 2/2011 | Childers et al. |
| 7,892,332 | B2 | 2/2011 | Prisco et al. |
| 2001/0042441 | A1 | 11/2001 | Purdom et al. |
| 2002/0156431 | A1 | 10/2002 | Feith et al. |
| 2003/0004492 | A1* | 1/2003 | Munis et al. ................ 604/503 |
| 2004/0019312 | A1 | 1/2004 | Childers et al. |
| 2004/0019313 | A1 | 1/2004 | Childers et al. |

| | | | | | |
|---|---|---|---|---|---|
| 2004/0197223 | A1* | 10/2004 | Olsen et al. | | 422/45 |
| 2005/0171491 | A1 | 8/2005 | Minh Miner et al. | | |
| 2005/0247203 | A1 | 11/2005 | Chevallet et al. | | |
| 2006/0137663 | A1 | 6/2006 | Vaught | | |
| 2008/0097315 | A1 | 4/2008 | Miner et al. | | |
| 2010/0217229 | A1 | 8/2010 | Miner | | |

FOREIGN PATENT DOCUMENTS

| | | |
|---|---|---|
| EP | 0106026 | 4/1984 |
| EP | 0143340 | 6/1985 |
| EP | 0318993 | 6/1989 |
| EP | 0350675 | 1/1990 |
| EP | 0501144 | 1/1992 |
| EP | 0587251 | 3/1994 |
| EP | 0808633 | 11/1997 |
| EP | 0776222 | 4/2003 |
| GB | 1408319 | 10/1975 |
| GB | 1554810 | 10/1979 |
| GB | 2061755 | 5/1981 |
| GB | 2212739 | 8/1989 |
| WO | 97/41904 | 11/1997 |
| WO | 9823353 | 6/1998 |
| WO | 2005089832 | 9/2005 |
| WO | 2006120415 | 11/2006 |

OTHER PUBLICATIONS

PCT Search Report issued Sep. 26, 2012 for Intl. Appln. No. PCT/US2011/067569.

Written Opinion issued Sep. 26, 2102 for Intl. Appln. No. PCT/US2011/067569.

* cited by examiner

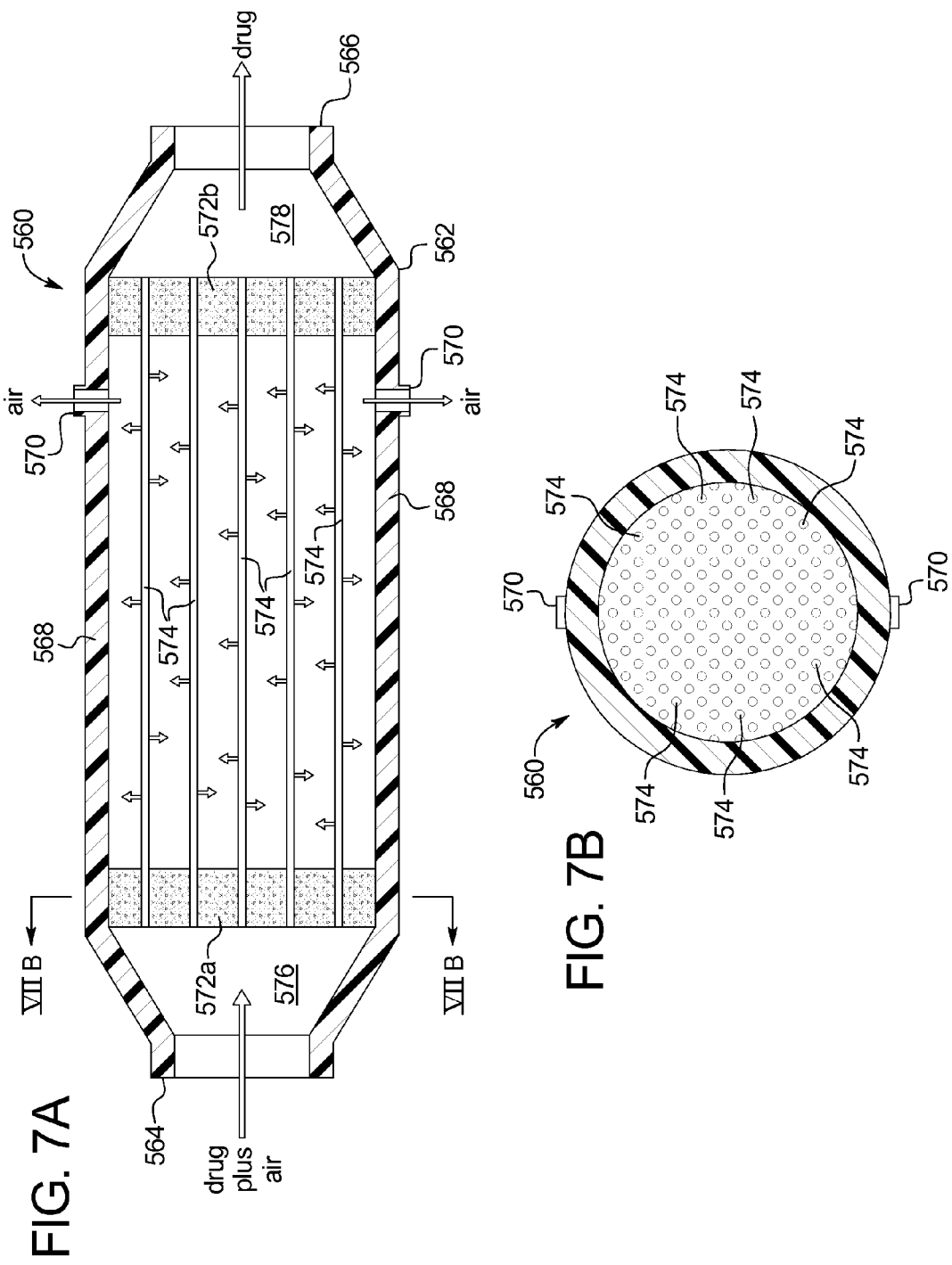

INTRAVENOUS PUMPING AIR MANAGEMENT SYSTEMS AND METHODS

BACKGROUND

The present disclosure relates generally to infusion pumping and in particular to air detection and elimination associated with infusion pumping.

Introduction of air into a patient's bloodstream via infusion pumping or drug delivery is a well known risk. Internationally recognized standards, such as IEC 60601, and recommendations from industry groups such as ECRI, call for infusion pumps to stop and alarm upon the detection of air bubbles of a minimum size, such as in the fifty to two-hundred fifty micro-liter ("μl") range. The interruption of drug delivery, however has its own significant drawbacks, such as interrupting the nurse or caregiver for the air-in-line event. The interruption can impact nursing labor hours and affect the overall provision of care. Also, the nurse's response can be delayed because of more pressing patient issues. There is also a risk of blood stream infection ("BSI") due to opening the intravenous ("IV") system to remove the air.

More importantly, stopping an IV drug infusion can lead to problems especially during a critical therapy, in the intensive care unit ("ICU") or during operating ("OR") environments, in which patients can be administered multiple IV medications, some of which are short acting drugs for which their flow stoppage can lead to blood pressure variation, arrthymia or other instability. The drugs are critical to the procedure or therapy being performed, which itself may be critical, leading to a negative situation when the IV pumping is stopped immediately after air-in-line detection.

An improved IV pump air management procedure is needed accordingly to avoid interruption of therapy.

SUMMARY

The present disclosure sets forth systems and methods for improved intravenous ("IV") pumping air management, which attempt to deliver uninterrupted infusion of critical IV liquids and medications even when air has entered the infusion line.

A first primary system and method includes an air removal device located upstream of the IV pump to prevent air from entering into the pump portion of the tubing set. In one embodiment, the pump is a shuttle type infusion pump, which uses upstream and downstream valves that sequence to allow medical liquid to be: (i) pulled into an area of the pump tubing set that operates with a shuttle pump actuator and then (ii) expelled from the section of pump tubing set. The air removal device can be made as part of the pump tubing set and is accordingly made of a suitable medical grade polymer or plastic. The air removal device can also have a housing positioned in-line with the pump tubing set, be a part of a pumping tubing set itself or be an enlarged diameter section of tubing connected in-line with the pump tubing set. The air removal device includes a liquid inlet and a liquid outlet and in an embodiment is disposed and arranged with respect to the pump tubing set so that in operation the liquid inlet resides elevationally above the liquid outlet.

An air passing but liquid retaining (e.g., hydrophobic) filter is located or carried by the air removal device at the top of the device, near the liquid inlet. A check valve is located in or carried by the air removal device in air flow communication with the hydrophobic filter. For example, the check valve could be located between (i) the hydrophobic filter and the external environment or (ii) just upstream of the hydrophobic filter. The check valve prevents the IV pump from drawing air through the hydrophobic filter into the air removal device when the IV pump is creating negative pressure to pull the drug or medical liquid from a supply into the pump.

A hydrophilic filter prevents any air in the air removal device from passing downstream into the pump tubing set. Collected air builds a slight pressure within the air removal device, eventually passing through the hydrophobic filter, cracking the check valve and leaving the air removal device and the IV system. Air is removed in a manner such that the pumping of the medical liquid or drug is not interrupted.

Liquid for pumping tends to pool at the bottom of the air separation device, at its liquid outlet. The liquid passing but air retaining (e.g., hydrophilic) filter is accordingly placed in one embodiment in the liquid outlet so that air that has not been removed from solution is trapped at the air retaining filter and is not allowed to pass to the pump actuation portion of the pump tubing set. As described in more detail below, the air removal devices of the present disclosure should be configured and arranged such that they are (i) not position sensitive or (ii) if position sensitive, arranged so that the hydrophobic membrane remains dry. That is, certain air removal devices described below are configured so that air can be removed from the devices regardless of their mounted orientation. But other devices described herein can become blocked such that they cannot purge when their hydrophobic membrane becomes wet. In this latter situation, the position sensitive devices are arranged on the infusion pump or elsewhere such that they do not allow the hydrophobic membrane to become blocked.

It is contemplated in one implementation to locate the air separation device upstream of the upstream shuttle pump valve in an attempt to allow only degassed medical liquid that has left the air separation device to enter the pump actuation portion of the pumping pump tubing set. Other alternative embodiments and structures for the first primary embodiment are discussed in detail below.

In a second primary embodiment, the air separation device moves the air removal device downstream of the pump actuator and eliminates the check valve, which is not needed because the downstream air removal device only sees positive pressure. The control unit of the infusion pump senses that the pump tubing set of this second embodiment has been loaded into the infusion pump and does not shut down the infusion pump upon the detection of air by an upstream air detector. The sensor can be positioned to sense the air removal device itself or a marking, e.g., a barcode on the pump tubing, which indicates the air removal device is present.

It is assumed that the downstream air removal device will remove air sensed by an upstream air removal device, however, a downstream air detector can also be provided. Thus when the upstream air detector detects air, the systems posts an alarm but does not stop the pump. If air is sensed at the downstream air detector, which has not been removed by the air separation device, the control unit shuts the infusion pump down via a valve located downstream of the downstream air detector.

If the air elimination device of the second primary embodiment (or any of the embodiments described herein) is position sensitive, an "air block" situation can occur. In such a situation, liquid wets the hydrophobic membrane, preventing or blocking air from thereafter being removed via the hydrophobic membrane. In such a situation, it is contemplated (i) to orient the air removal device in a vertical manner (e.g., by vertical placement in the pump housing), such that air migrates to the top of the air removal device where the hydrophobic vent is located to purge the air, or (ii) to otherwise orient the air removal device to direct air bubbles to the hydrophobic membrane or vent.

In a third primary system and method of the present disclosure, air that is detected is actively purged from the pumping system in a manner such that the pumping of the medical liquid or drug is not interrupted. The IV pump in one implementation is again a shuttle type medical infusion pump. Here, an additional air purge valve is added downstream of the downstream shuttle pump valve. An air removal device is placed in liquid communication with the pump tubing set between the downstream shuttle pump valve and the even further downstream additional air purge valve. The air removal device of this third primary embodiment can include a separate housing that is teed-off or that otherwise extends from the pump tubing set located between the downstream valves. The housing may simply be a port that supports the liquid retaining or hydrophobic filter or membrane. A hydrophilic filter is not needed with the air removal device of the third primary embodiment.

A bypass line is provided that extends from a point in the tubing between the downstream air removal device and the downstream additional air purge valve back to a point upstream of an air removal device that itself is upstream of the pump. A bypass valve is provided in the bypass line. Under normal operation when no air is present, the downstream additional air purge valve is opened and the bypass valve is closed, allowing fluid to be pumped to the patient.

If air is detected in the pump tubing set, the additional downstream air purge valve is closed and the bypass valve is opened, creating pressure between the shuttle pump actuator and the closed, additional downstream valve, and causing air entrained fluid to flow back upstream of the pump. The pressure and recirculation forces air into the air removal device and out of a vent or valve, e.g., an air passing but liquid retaining or hydrophobic filter or membrane attached to the air removal device. The downstream air purge valve can be closed and the bypass valve opened for an amount of time or a number of pump-out strokes that is known or expected to be sufficient to purge air from the system, or until an air sensor measurement is "cleared", after which the air purge valve is opened and the bypass valve is closed to allow the pressurized and degassed medical liquid or drug to flow towards the patient.

Multiple configurations of the air eliminating device are possible with the bypass recirculation of the third to fifth primary embodiment. The air removal devices are not position sensitive in one preferred embodiment. If the air elimination device is position sensitive, it should again be oriented in a vertical manner (e.g., located as such by placement in the pump housing) or be implemented with a configuration that will direct air bubbles to the hydrophobic element. Also, with any of the recirculation bypass embodiments, it is contemplated to run the infusion pump as quickly as possible in the recirculation bypass air elimination mode, so as to minimize the time during which medication is not delivered to the patient and to remove air as quickly and effectively as possible.

In a fourth primary embodiment, a bypass recirculation line and bypass valve are again provided but no hydrophobic filter, hydrophilic filter or check valve is needed. The additional downstream air purge valve of the third primary embodiment is also provided. The valved bypass or return line is runs again from a point in the main therapy tubing between the downstream valves, back to a supply bag or supply container. The supply container is thus connected to two lines, the main therapy line and the return bypass line. When air is detected by an upstream air sensor, the furthest downstream air purge valve actuator closes, the bypass valve actuator opens, the pump actuator and associated valve actuators continue to operate, and air entraining medical fluid is recirculated back through the supply container. Recirculation can be controlled via feedback, in which it is continued until the upstream air detector no longer senses air, or be controlled open loop, e.g., for a period of time or number of pump strokes. The downstream air detector operates as a fail-safe system shut down detector.

In a fifth primary embodiment, a recirculating bypass line, bypass valve and downstream air purge valve are again provided. Here, like with the third primary embodiment, the bypass line returns to the main therapy tubing instead of to the supply container. Also, a hydrophobic air removal device is placed either in the main flow therapy tubing or in the bypass line. In one example, the air removal device is a centripetal air removal device that can be placed anywhere in the bypass line. When the upstream air sensor detects air, the air purge valve actuator closes and the bypass valve actuator opens, while the pump actuator and associated valve actuators continue to operate. The air entraining medical fluid is recirculated, closed loop or open loop as described herein, until air has been satisfactorily removed from the medical fluid. The downstream air detector operates again as a fail-safe sensor to shut the system down if needed.

In a sixth primary embodiment, a highly effective hydrophobic air removal device, described herein as a hydrophobic, air removal dialyzer is located between the downstream pump valve actuator and a downstream air detector. The efficient hydrophobic air removal device includes a housing with potted ends that hold long, thin hydrophobic fibers, forming a structure having a look similar to a dialyzer. The housing defines one or more air vents. Medical fluid possibly entraining air flows through the insides of the hollow hydrophobic fibers. The elongated geometry and narrow lumens of the fibers and an overall positive transmembrane pressure tending to push air radially out of the fibers provides a path of resistance for the entrained air radially out of the fibers that is much less than the resistance required to flow all the way through the fibers. It is accordingly believed that such air removal device may be efficient enough not to require an accompanying hydrophilic membrane, air purge valve or bypass path. A downstream fail-safe system shutdown air sensor is provided in an embodiment in case air does escape through the exit end of the dialyzer-like air removal device.

There are a number of features applicable to each of the primary embodiments discussed herein. For example, each of the embodiments discussed herein provides a first air-in-line detector placed upstream of the pump actuation area of the pump tubing set to detect air prior to the air reaching the pump. The upstream air sensor and any of the air sensors discussed herein can for example be ultrasonic air detector that uses ultrasonic waves to non-invasively detect air bubbles flowing inside the tube. For any of the embodiments discussed herein, the upstream air detector may additionally be used with the associated control unit to integrate the sensed air over time, so that the accumulated air can be subtracted from an assumed amount of total fluid pumped, which may be assumed by counting pump strokes of known volumes. It is contemplated to use an air detector that can estimate the size of the air bubbles so that the air volume can be accumulated. It is also contemplated to use multiple air detectors, e.g., spaced ninety degrees from each other to detect each of a pair of air bubbles traveling together.

Also, a second, downstream air detector may be provided to ensure that the system and method has removed the air detected by the upstream air sensor. In particular, the second primary embodiment places the downstream air detector upstream of a downstream valve actuator as discussed below. The other primary embodiments may place a downstream air detector much closer to the patient. It is contemplated to configure the control unit such that the pump is allowed to continue to pump the drug or medication to the patient until the air detected by this downstream sensor is calculated to be close to the infusion site based for example on a known flowrate, tubing diameter, tubing length and location of the activated air detector. Such structure and methodology again maximizes the time that the drug is delivered to the patient, while maintaining safety.

Alternative embodiments and structures for the air removal devices are described in detail below, including combinations of the systems and methods of the primary embodiments.

It is accordingly an advantage of the present disclosure to provide intravenous ("IV") pump air removal systems and methods.

It is another advantage of the present disclosure to provide air removal systems and methods that do not require the pump to interrupt therapy for situations in which air is introduced into an intravenous line.

It is a further advantage of the present disclosure to provide air removal systems and methods that remove air from the medical liquid or drug prior to reaching the pump.

It is still another advantage of the present disclosure to provide IV pump air removal systems and methods that actively purge air that travels downstream of the infusion pump.

It is yet a further advantage of the present disclosure to provide IV pump air removal systems and methods that use a highly efficient in-line hydrophobic air removal device.

Additional features and advantages are described herein, and will be apparent from the following Detailed Description and the figures.

BRIEF DESCRIPTION OF THE FIGURES

FIG. 7A is a sectioned front elevation view of one embodiment of the hydrophobic, air removing dialyzer or device of FIG. 6.

FIG. 7B is a sectioned end view taken along line VIIB-VIIB of FIG. 7A.

DETAILED DESCRIPTION

System Generally

Figure 1:
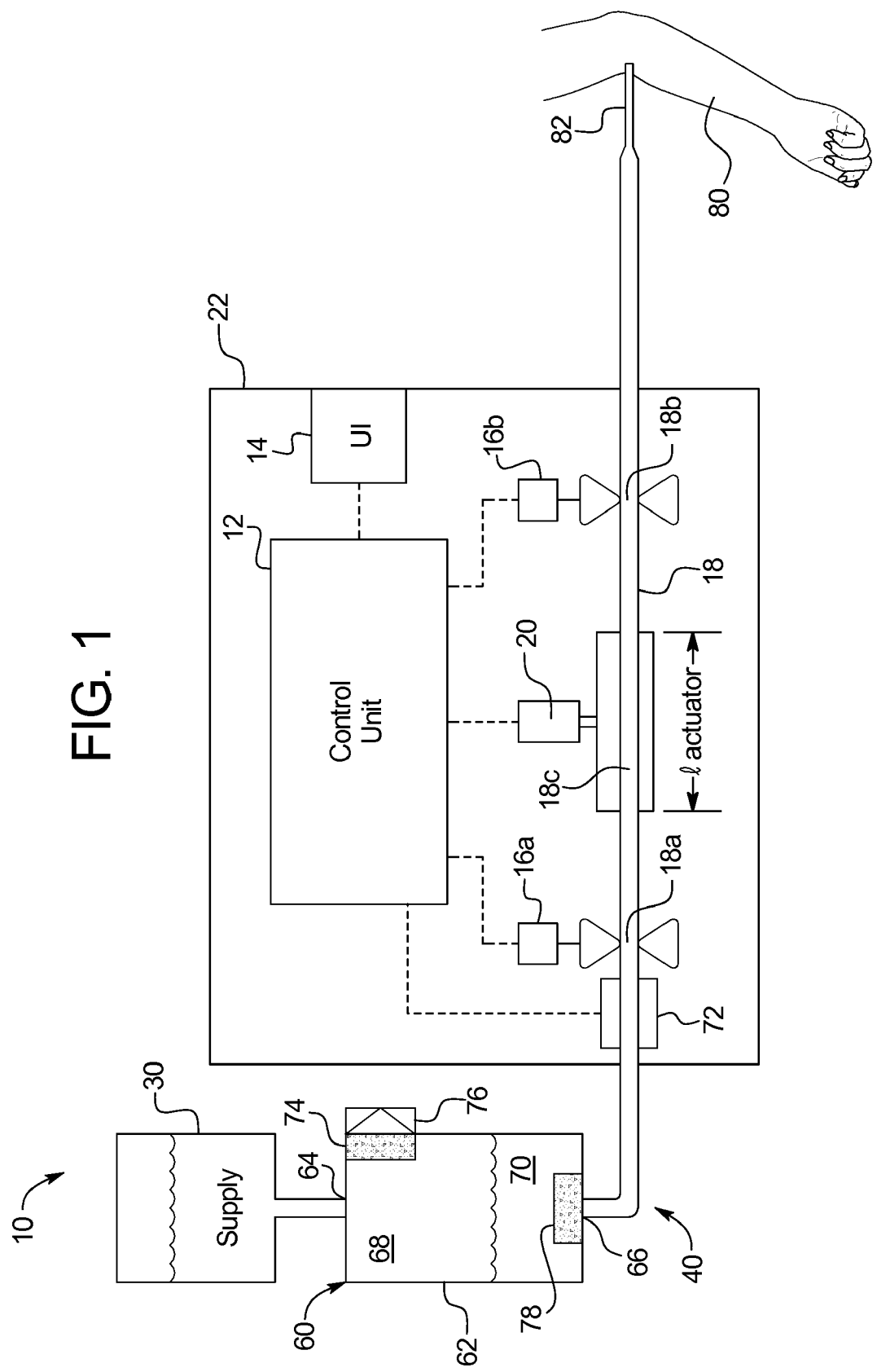
FIG. 1 is a schematic view of one embodiment of an intravenous ("IV") pumping system and method of the present disclosure having an upstream air removal apparatus.

Referring now to the drawings and in particular to FIG. 1, intravenous ("IV") pumping system 10 illustrates one primary embodiment of the air removal apparatus and methodology of the present disclosure. IV pumping system 10 pumps a medical liquid, drug or medicament from a supply 30, through a tube 18, to a patient 80, via a patient catheter, needle or cannula (catheter 82 used hereafter to represent all) 82. Tube 18 and an air removal device, such as device 60 of FIG. 1, form part of one embodiment of an IV pump tubing set 40. Tubing set 40 in an embodiment is then connected to supply 30 and catheter 82 to form an overall disposable component of system 10. Tube 18 as illustrated is loaded into IV pumping system 10, so that IV pumping system 10 can pull liquid from supply 30 and move the liquid in a controlled manner through tube 18, catheter or cannula 82 to patient 80.

IV pumping system 10 includes a control unit 12. Control unit 12 includes one or more processors, such as supervisory processor, which controls one or more delegate processors, which in turn controls various aspects of IV pumping system 10. Control unit 12 can, for example, employ a safety or monitoring processor, which ensures that the supervisory processor and delegate control processors are operating properly. The processors operate with one or more memory, which is also part of control unit 12. As shown, control unit 12 operates with or controls a user interface 14. The user interface 14 displays information to the patient or operator and also allows the patient or operator to enter information from the user interface into control unit 12. To that end, user interface 14 can operate with a touch screen overlay or with one or more electromechanical input device, such as a membrane switch.

User interface 14 enables the operator to command control unit 12 to control IV pumping system 10 to run: (i) a continuous mode in which pump 10 delivers liquid via tubing 18 to achieve a desired volume at a single flowrate; (ii) an auto-ramp mode in which IV pumping system 10 delivers liquid from supply 30 at a rate that gradually increases to a threshold, remains at the threshold rate for a prescribed time, and then gradually decreases; (iii) an intermediate mode in which IV pumping system 10 delivers discrete liquid volumes spaced over relatively long periods of time, such as a bolus or volume every three hours; (iv) a custom mode in which IV pumping system 10 delivers a unique infusion rate at different time intervals; (v) a patient-controlled analgesic ("PCA") mode during which patient 80 presses a button causing IV pumping system 10 to periodically infuse a bolus of analgesic into the patient; and (vi) a closed loop therapy mode based on physiological sensor feedback. User interface 14 can display one or more features and parameters pertinent to the air management systems operation, such as an amount of air detected and removed from pump tubing set 40 and the therapy time or log of air removed events.

To provide the various modes of delivery, control unit 12 operates an upstream valve or occluder 16a, a downstream valve or occluder 16b and a pump actuator 20. Valves or occluders 16a and 16b are shown as being electrically actuated pinch or solenoid valves but can alternatively be pneumatically or pneumatic/mechanically actuated membrane valves or pillow valves. To this end, while the IV pump tubing set 40 is shown to use tube 18 for valving and pumping, a pumping and valving cassette, e.g., for pneumatic or pneumatic/mechanical operation, can be used alternatively. Control unit 12, user interface 14, valve actuators 16a and 16b, and pump actuator 20 in the illustrated embodiment are housed in pump housing 22.

In one embodiment, the systems and methods described herein operate with a shuttle pump type of pump actuator. One suitable shuttle pump type of pump actuator is set forth in U.S. Pat. No. 5,842,841, entitled, "Volumetric Infusion Pump With Transverse Tube Loader", assigned to the assignee of the present disclosure, the entire contents of which are incorporated herein by reference and relied upon. Other embodiments of the systems and methods of the present disclosure, however, can use volumetric membrane type pumps, peristaltic or other types of roller pumps.

With a shuttle pump or volumetric membrane pump, to pump a known volume of drug or medicament, control unit 12 causes valve or occluder 16a to pinch or compress an upstream valve portion 18a of tubing 18 upstream of pump actuator 20. Control unit 12 also causes valve or occluder 16b to open and at the same time or slightly thereafter cause pump actuator 20 to compress tubing 18 at pump actuation portion 18c, forcing a known volume of liquid residing in tubing 18 through downstream valve portion 18b of tubing 18, towards catheter or cannula 82 and patient 80. The known volume of liquid is set by a length $l_{actuator}$ of the clamping portion of the pump actuator 20 multiplied by an internal cross-sectional area of tubing 18 at pump actuation portion 18c.

After the drug or medicament volume is delivered to patient 80, control unit 12 causes downstream valve or occluder 16b to close downstream valve portion 18b and simultaneously or slightly thereafter open valve actuator 16a, allowing medical liquid from supply 30 to flow through downstream valve portion 18b of tubing 18 into pump actuation portion 18c of tubing 18. Pump actuator 20 is simultaneously or slightly thereafter opened to indirectly or actively decompress tubing portion 18a, creating a vacuum, which draws the drug or medicament into pumping portion 18c within the length $l_{actuator}$ of the clamping portion of pump actuator 20. Gravity may help feed the medical liquid or drug from supply 30 into pumping portion 18c of tubing 18, however, it is not typically relied upon.

Control unit 12 repeats the above-described valve sequencing and pump actuation until a desired total amount of medical liquid is delivered via cannula or catheter 82 to patient 80. The total volume is equal to the individual pump volumes of pumping portion 18c multiplied by the number of pump-out strokes. The rate at which valves 16a and 16b are switched in combination with the actuation of pump actuator 20 sets the rate at which the drug, medicament or medical liquid is delivered to patient 80.

First Primary Embodiment

In system 10 of FIG. 1, an air removal device 60 is located upstream of valve actuator 16a and corresponding upstream valve portion 18a of tubing 18. Air removal device 60 may be located along IV pump tubing set 40, such that the device resides inside or outside of pump housing 22. Air removal device 60 includes its own housing 62, e.g., of a rigid construction, which in one embodiment is made of a medical grade polymer, which can be relatively inexpensive, especially for the case in which air removal device 60 is integral with and disposed with IV pump tubing set 40. Air removal device 60 may be made for example of the same material as tubing 18, such as, silicone, polyvinyl chloride ("PVC") or other materials whose selection can be optimized for a particular use.

Housing 62 can be a cylindrical, rectangular or other suitably shaped container and be made of a semi-rigid or rigid material such as polycarbonate and acrylonitrile butadiene styrene ("ABS"). Housing 62 in one preferred embodiment is cylindrical with smooth geometric transitions to route liquid without causing air entrainment in the fluid. Housing 62 can be a larger diameter section of tubing than tubing 18. Housing 62 can further alternatively be a section of tubing having a same diameter as tubing 18. Still further alternatively, housing 62 has a "Y" or "T" extension protruding from housing 62 at an angle to or perpendicular from the axis of tubing 18. Housing 62 in one embodiment is configured to be easily sterilized using the appropriate materials and methods, such as gamma radiation or electron beam sterilization.

Housing 62 of air removal device 60 includes a liquid inlet 64 and a liquid outlet 66. An air collection portion 68 of housing 62 resides in the illustrated embodiment adjacent to liquid inlet 64. In use, air collection portion 68 will operate even if completely filled with liquid. Alternatively, air collection portion 68 may reside at the end of a "Y" or "T" extension (not illustrated) protruding from a main body portion of housing 62. A liquid collection portion 70 of housing 62 resides adjacent to liquid outlet 66.

As shown in the illustrated embodiment, air removal device 60 in one embodiment is configured such that air collection portion 68 resides, in operation, elevationally or vertically above liquid collection portion 70. In operation, medical liquid or drug flows from supply 30, through liquid inlet 64 of housing 62 and settles in liquid collection portion 70. Air rises through the liquid of liquid collection portion 70, degassing out of solution and settling within air collection portion 68 of housing 62 before being forced out of air removal device 60.

An air passing but liquid retaining filter 74, e.g., a hydrophobic filter, is fitted to or formed with housing 62 at the air collection portion 68 of air removal device 60. One suitable hydrophobic material for hydrophobic filter 74 is a "super hydrophobic" filter, which can be a polyvinylidene fluoride ("PVDF") material grafted with a fluorinated monomer, such as a REPEL™ filter made by Millipore, 290 Concord Road, Billerica, Mass. 01821. Filter 74 in one advantageous embodiment is located below the supply as far as possible and as close as possible to the pump, so as to maximize gravity head pressure to operate rack open the normally closed one-way check valve 76.

While it is desirable to align housing 62 of air removal device 60 with pump housing 22 vertically as shown in FIG. 1, such that liquid retaining filter 74 is located elevationally above outlet 66, it is also desirable to design the geometry of the housing and the placement of the filters such that the device is as position insensitive as possible. A "super hydrophobic" filter 74 is more position insensitive than one that is not because it is less prone to wetting out.

Another possibility for making liquid retaining filter 74 more position insensitive is to use a filter provided by Ivax Corporation, Miami Fla., which combines a hydrophilic element (discussed below) with a hydrophobic element. A further possibility for making liquid retaining filter 74 more position insensitive is to use a device provided by Gelman, Inc, Ann Arbor Mich., Part Number 6164420, which is a device that sandwiches two liquid retaining (hydrophobic) filters 74 around a single hydrophilic element (discussed below).

In still another alternative embodiment, housing 62 is structured to provide an annular, circular or spherical liquid path around liquid retaining filter 74. Assuming the flowrate (e.g., a bypass or recirculation flowrate as shown below in FIG. 5) of the medical liquid to be sufficient, such as 1000 to 4000 milliliters/hour, the heavier liquid tends to be pushed by centripetal force outwardly along the annular or circular liquid path, causing the air to migrate inwards towards liquid retaining filter 74. It is contemplated that liquid retaining filter 74 could extend horizontally or vertically (or even at some angle) relative to the annular or circular liquid path, so as to make air removal device 60 less position sensitive.

In the illustrated embodiment, a one-way check valve 76 is provided with housing 62 just outside of liquid retaining filter 74. Alternatively, liquid retaining filter 74 is provided with housing 62 just outside of one-way check valve 76. Check valve 76 can be a normally closed one-way duckbill check valve as shown in FIG. 1, a spring-loaded ball valve or a spring-loaded flapper valve. For example, housing 62 can provide an aperture to which liquid retaining filter 74 is abutted against the inside of the housing. A spring-loaded flap is provided on the outside of the aperture and housing 62. Positive pressure forces the flap open to relieve air through liquid retaining filter 74. Negative pressure inside housing 62 and the spring force (e.g., due to a natural bias of a living hinge connecting the flap to housing 62) seals the flap closed against the outside of housing 62. In any case, check valve 76 prevents air from being pulled into housing 62 when pump actuator 20 creates negative pressure in the fill portion 18c of tubing 18.

In an embodiment, check valve 76 requires a low cracking pressure of, e.g., on the order of ten inches of water pressure. Suitable check valves are provided by Nipro Medical Corporation, 3150 NW 107th Avenue, Miami, Fla. 33172. The cracking pressure may be reached naturally due to the head height of the fluid in the supply container, with air building within air collection portion 68 or may occur with the aid of upstream collection valve 16a closing, forcing a small amount of medical liquid back towards air removal device 60. Check valve 76 as discussed prevents air from being pulled into air removal device 60 through liquid retaining filter 74, especially when pump actuator 20 opens to create a negative pressure within housing 62.

In the illustrated embodiment, a liquid passing but air retaining filter 78, e.g., a hydrophilic filter, is fitted to or formed with housing 62 at or near the liquid outlet 66 to prevent air from exiting though outlet 66 into downstream tubing 18. Suitable air retaining filters 78 can again be obtained for example from Millipore, 290 Concord Road, Billerica, Mass. 01821, e.g., MF-Millipore™ membranes, Millipore Express® membranes and PVDF membranes. Filter 78 separates the air from the liquid drug, so that the air can be collected in air collection portion 68 and forced out of air removal device 60 through liquid retaining filter 74 and check valve 76 or vice versa.

In the illustrated embodiment, retaining filter 78 is shown as a flat sheet. In an alternative embodiment, hollow fiber dialyzer or hemofilter type microporous membranes are provided and are looped such that both ends of each hollow fiber are encased into a potting material placed in outlet 66. The potting material encases only the exterior of the hollow fibers; the lumens of the hollow fibers are not encased and are in communication with outlet 66. Thus any fluid making its way through the air removal device 60 has to flow through the pores of one of the looped hollow fiber membranes. The microporous membranes when wetted however block air from migrating through the membranes, as is known, thereby acting to separate or degas the air from the liquid drug. Only the liquid medical fluid can therefore make its way through the air removal device 60 and into pump tubing 18.

It is contemplated to size housing 62 such that air collection portion 68 is large enough to collect all air degassed by hydrophilic or air retaining filter 78. Here, liquid retaining filter 74 and check valve 76 may not be needed.

In system 10 of FIG. 1, an air detector 72, is placed downstream of air removal device to detect any air that for some reason is not removed from solution and enters pump tubing 18. Air sensor 72 can be a non-invasive ultrasonic air sensor, such as those described in U.S. Pat. Nos. 4,607,520, 4,651, 555 and 7,661,293. In the illustrated embodiment, air sensor 72 is located upstream of valve actuation portion 18a of tubing 18, so that valve 16a can be clamped if air is detected prior to the air entering pump actuation portion 18c of tubing 18. Air sensor 72 is located alternatively (or a second air sensor is added) downstream of valve actuation portion 18c of tubing 18 as a last chance check to make sure pumping is stopped if air that is about to go to the patient is detected.

Second Primary Embodiment

Figure 2:
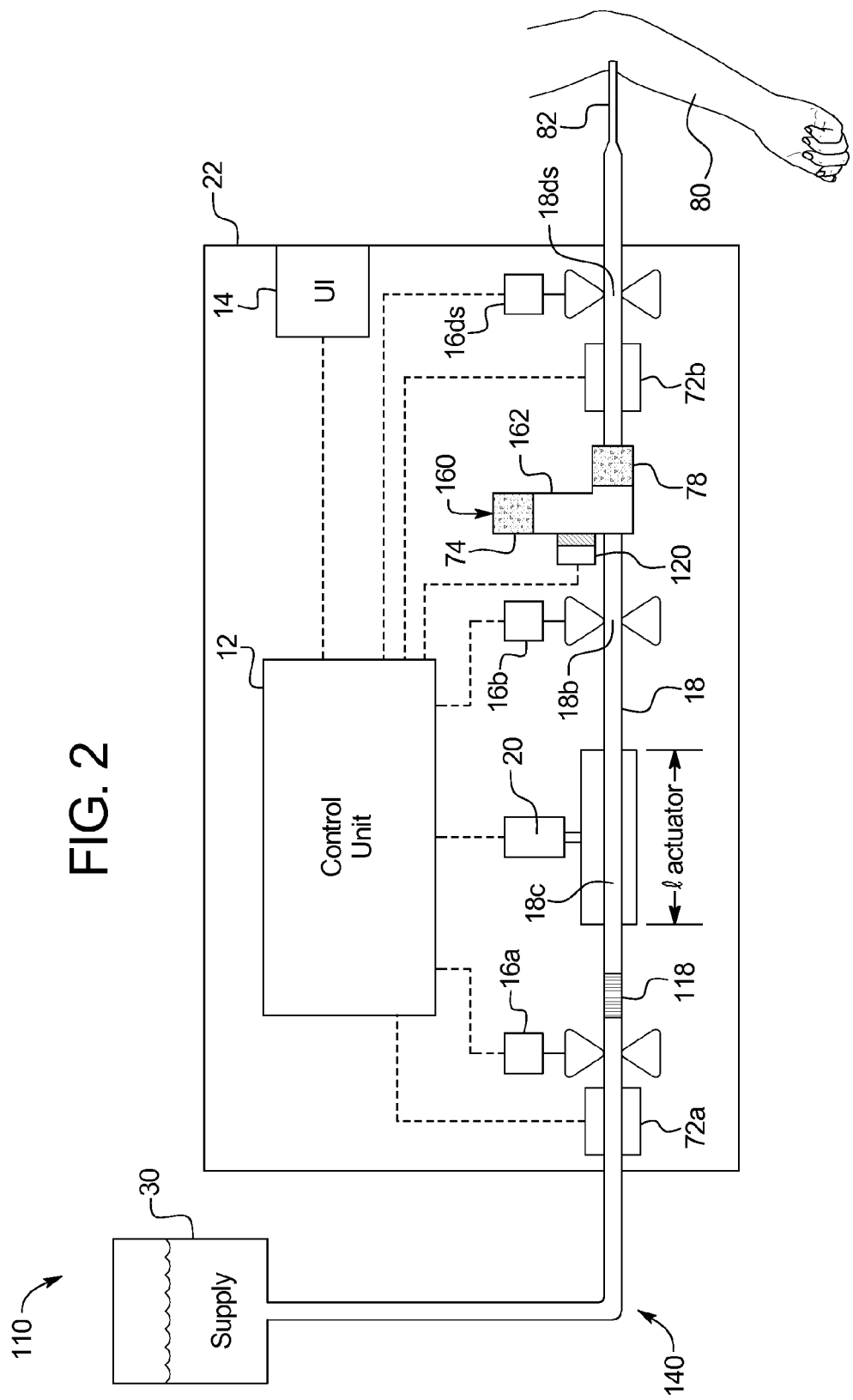
FIG. 2 is a schematic view of one embodiment of an IV pumping system and method of the present disclosure having a downstream air removal apparatus.

Referring now to FIG. 2, system 110 is an alternative air removal system to system 10. System 110 is similar in many respects to system 10 of FIG. 1 and like structures are provided with the same element numbers. System 110 provides upstream and downstream air detectors 72a and 72b, respectively. Upstream air removal device 60 is not used and instead a downstream air removal device 160 is provided, which includes a housing 162 (made of any of the materials for housing 62) having a liquid retaining filter 74, such as a hydrophobic filter, and an air retaining filter 78, such as a hydrophilic filter. Air removal device 160 may be position sensitive, that is, hydrophobic filter 74 may be prone to becoming wetted, causing an air block. In such a case, air removal device 160 is mounted vertically as shown, such that liquid retaining filter 74 resides at the top of housing 162.

Air retaining filter 78 separates air from the liquid and liquid retaining filter 74 vents the air to atmosphere. Because downstream tubing 18b is never intended to be under negative pressure, the check valve 76 of FIG. 1 is not needed. However, if desired, a check valve could be added to air removal device 160 as an additional safety measure. A further downstream air purge valve actuator 16ds, operable with downstream pump tubing portion 18ds, is added in one embodiment. Downstream valve actuator 16ds also communicates with control unit 12.

In the illustrated embodiment, a sensor 120, such as a capacitive or inductive magnetic sensor, an optical sensor, or an electro-mechanical sensor, in communication with and possibly powered by control unit 12, is located within housing 22 so as to sense or not sense the presence of air removal device 160. In an alternative embodiment, sensor 120 is a reader that reads a marking 118 (shown in FIG. 2). Marking 118 can be a barcode or radio frequency identification ("RFID") tag located on either tubing 18 or housing 162 that is read by a suitable reader 120, such as a barcode or RFID reader. Marking 118 identifies pump tubing set 140 as one that does or does not contain air removal device 160.

Sensor or reader 120 communicates data or electrical signals with control unit 12, letting control unit 12 know that an air removal device 160 is in place. Control unit 12 is likewise programmed to know that air sensed at upstream air detector 72a is not to be taken as an event that shuts down system 110, e.g., closes furthest downstream valve actuator 16ds, shuts down pump actuator 20 and/or closes one or both of valve actuators 16a and 16b. That is, it is expected that air removal device 160 will remove air sensed at air detector 72a.

If air is sensed at downstream detector 72b, however, then control unit closes furthest down stream valve actuator 16ds so as to prevent air from reaching patient 80. Control unit 12 can likewise shut down pump actuator 20 and close one or both of valve actuators 16a and 16b. If (i) sensor 120 does not sense air removal device 160, (ii) if the alternative marking 118 otherwise indicates that pump tubing set 140 is not one that includes an air removal device 160, or if (iii) in the alternative marking embodiment no marking 118 is detected at all, control unit 12 is programmed to instead shut down the pump and valve actuators when air is detected at upstream air detector 72a.

Third Primary Embodiment

Figure 3:
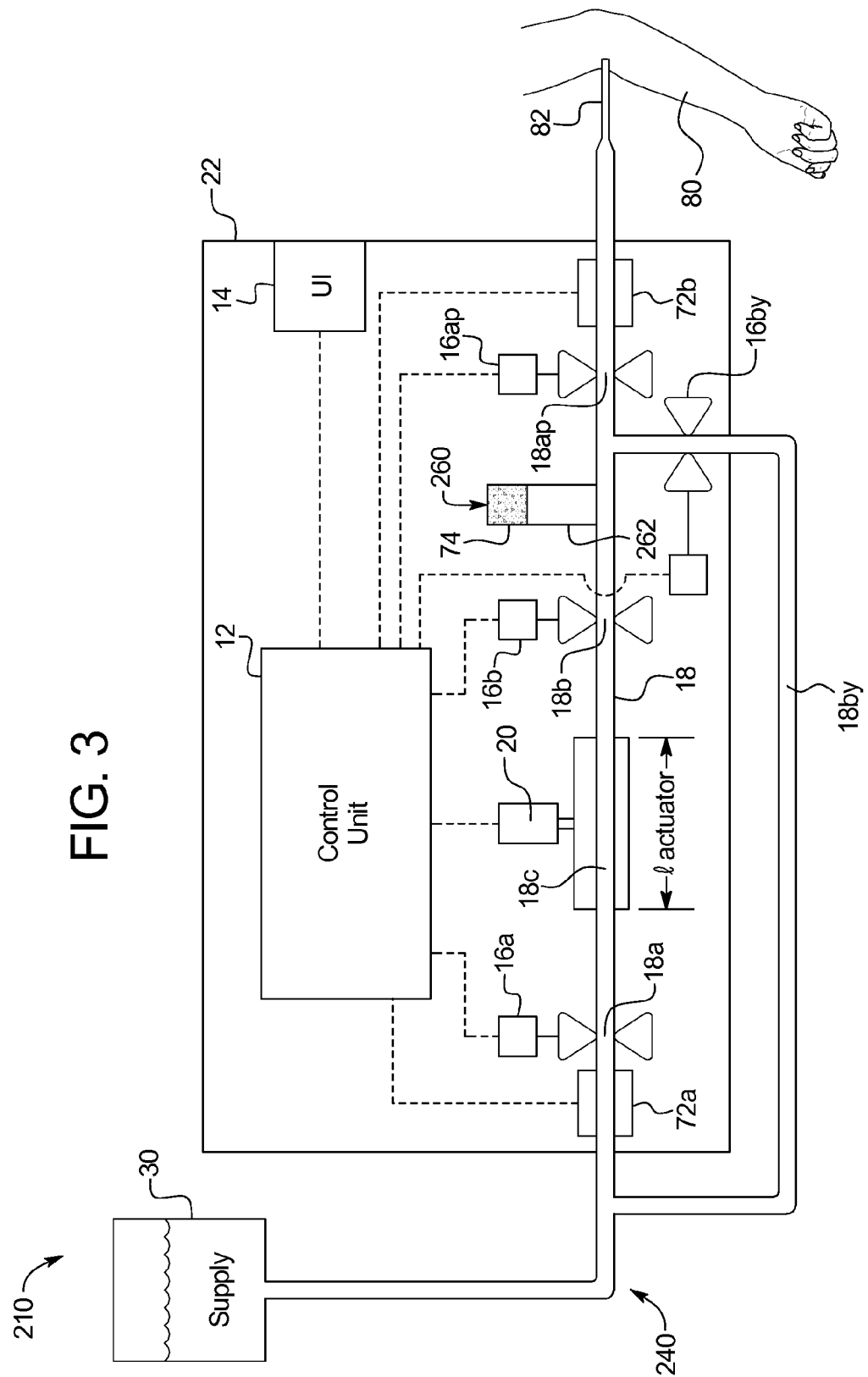
FIG. 3 is a schematic view of one embodiment of an IV pumping system and method of the present disclosure having an air removal recirculation bypass apparatus.

Referring now to FIG. 3, system 210 illustrates a first alternative embodiment for an IV pumping system and method having air removal management using a bypass return line. System 210 pumps medical liquid in the same way, using the same apparatuses housed in pump housing 22 operating with an IV pump tubing set 240, including all alternatives for these apparatuses discussed herein.

System 210 also includes an air removal device 260. Air removal device 260 includes a body 262, which in the illustrated embodiment is a "T" off of main therapy flow line 18. Body 262 is alternatively a "Y" off of main therapy flow line 18, a larger diameter cylindrical or rectangular housing, a larger diameter piece of tubing, or a piece of tubing having a same diameter as tubing 18. Body 262 includes, forms or otherwise houses an air passing but liquid retaining filter 74, e.g., a hydrophobic filter. Air passing but liquid retaining filter 74 can be of any of the types described herein. Air removal device 260 is either position insensitive or mounted such that liquid retaining filter 74 does not become wetted.

System 210 further includes a bypass line 18*by* and corresponding bypass valve actuator 16*by*. Bypass line 18*by* branches off of main tubing line 18 from a point between air removal device 260 and air purge valve actuator 16*ap* and returns fluid to main tubing line 18 upstream of upstream air sensor 72a. Air removal device 260 can be placed alternatively in bypass line 18*by*.

Air removal device 260 is located in, e.g., formed with or connected to, tube 18 of IV pump tubing set 240 between downstream valve actuator 16*b*/downstream valve portion 18*b* of tube 18 and a further downstream, air purge valve actuator 16*ap*, which operates with a corresponding portion of tubing 18*ap*. Bypass valve actuator 16*by* and air purge valve actuator 16*ap*, like the other valve and pump actuators described herein, are controlled by control unit 12 and can be of any of the types described above for valve actuators 16*a* or 16*b*. Control unit 12 also powers and receives signals from upstream air sensor 72a and downstream air sensor 72b. Air sensors 72a and 72b can again be non-invasive ultrasonic air sensors, such as those described in U.S. Pat. Nos. 4,607,520, 4,651,555 and 7,661,293.

During normal pumping operation, if upstream air sensor 72a detects air in tubing 18, an appropriate signal is sent to control unit 12. Control unit 12, which maintains air purge valve actuator 16*ap* in an open, e.g., energized state, and bypass valve actuator 16*by* in a closed, e.g., un-energized, state during normal pumping operation, closes, e.g., un-energizes, air purge valve actuator 16*ap* and opens, e.g., energizes, bypass valve actuator 16*by* when air sensor 72a senses air. When air purge valve actuator 16*ap* is closed and bypass valve actuator 16*by* is opened, pumping valve actuators 16*a* and 16*b* and pump actuator 20 perform at least one pump-out stroke and in an embodiment a series of full pumping strokes. This action circulates air entraining medical fluid through main flow tubing 18 and bypass line 18*by* to remove air through air removal device 260.

In one embodiment, control unit 12 is configured to monitor air sensor 72a and maintain the bypass valve and air purge pumping state until air sensor 72a indicates that the main flow of medical fluid no longer entrains air. Here, air sensor 72a is used as a feedback provider to control unit 12. Control unit 12 is alternatively configured to run open-loop and maintain this air purge recirculation state for an amount of time or number of pump strokes that is known or expected, e.g., determined empirically, to satisfactorily drive air out of air removal device 260. Downstream air detector 72b may again be provided to ensure that air has been removed once air purge valve actuator 16*ap* is opened to resume pumping and to shut system 210 down if air detector 72b senses air.

It is expected that because air removal device 260 is not typically under negative pressure in its location between pump portion 18*c* and portion 18*ap*, that air removal device 260 does not need a check valve as provided above for system 10. If desired however, a check valve can be provided.

As discussed above, it is also contemplated to provide combinations of the systems described herein. For example, in FIG. 3 air removal device 60 of systems 10 could be provided in addition to air removal device 260 and air purge valve actuator 16*ap*. Here, air removal device 60 is provided to capture and purge air before the air reaches upstream sensor 72a. If air somehow migrates past first air removal device 60, then second air removal device 260, valve actuators 16a and 16b, and air purge valve actuator 16*ap* operate as described to eliminate the downstream sensed air. Likewise, air removal device 160 of system 110 could be provided as a safety in case air removal device 60 did not remove all air.

Fourth Primary Embodiment

Figure 4:
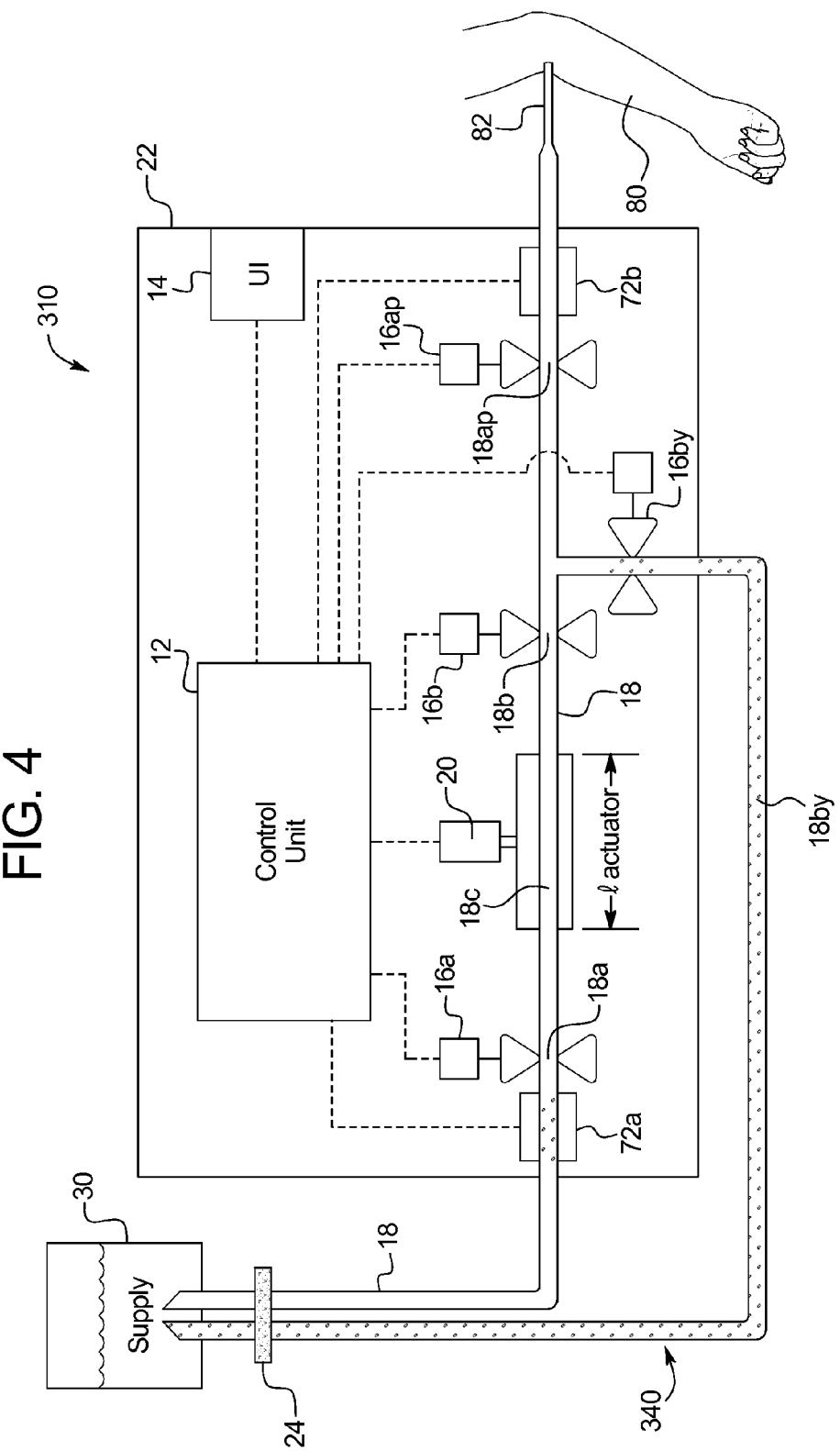
FIG. 4 is a schematic view of another embodiment of an IV pumping system and method of the present disclosure having an alternative air removal recirculation bypass apparatus.

Referring now to FIG. 4, system 310 illustrates another alternative embodiment for an IV pumping system and method having air removal management. System 310 pumps medical liquid in the same way, using the same apparatuses housed in pump housing 22 operating with an IV pump tubing set 340, including all alternatives for these apparatuses discussed herein.

System 310 in the illustrated embodiment does not include an air removal device having a hydrophobic and/or hydrophilic filter as do the systems above. System 310 does provide the third air purge valve actuator 16*ap* described above in connection with system 210 of FIG. 3, which operates with a corresponding portion of tubing 18*ap*. Control unit 12 of system 310 also powers and receives signals from upstream air sensor 72a and downstream air sensor 72b. Air sensors 72a and 72b can again be non-invasive ultrasonic air sensors, such as those described in U.S. Pat. Nos. 4,607,520, 4,651,555 and 7,661,293.

IV pump tubing set 340 includes a bypass line 18*by*, which returns from a point in the main flow tubing 18 between valve portion 18*b* and valve portion 18*c* to fluid supply 30. In the illustrated embodiment, bypass line 18*by* is coupled with the main supply line 18 via a dual lumen spike 24 to simultaneously pierce or otherwise make fluid communication with fluid supply 30. Bypass line 18*by* enables air entraining medical fluid to be returned to fluid supply 30, so that the air can be collected at the top of the fluid supply.

An additional bypass valve actuator 16*by* is provided and controlled by control unit 12. Bypass valve actuator 16*by* as illustrated occludes or opens a portion of bypass line 18*by*.

During normal pumping operation, if upstream air sensor 72a detects air in tubing 18, an appropriate signal is sent to control unit 12. Control unit 12, which maintains air purge valve actuator 16*ap* in an open, e.g., energized state, and bypass valve actuator 16*by* in a closed, e.g., un-energized, state during normal pumping operation, closes, e.g., un-energizes, air purge valve actuator 16*ap* and opens, e.g., energizes, bypass valve actuator 16*by* when air sensor 72a senses air. When air purge valve actuator 16*ap* is closed and bypass valve actuator 16*by* is opened, pumping valve actuators 16*a* and 16b and pump actuator 20 perform at least one pump-out stroke and in an embodiment a series of full pumping strokes. This action circulates the air entraining medical fluid through main tubing 18, bypass line 18by and fluid supply 30.

Control unit 12 is configured to monitor air sensor 72a and maintain the bypassing valve and air purge pumping state until air sensor 72a indicates that the medical fluid does not have air. In this instance, air sensor 72a is used as a feedback provider to control unit 12 Control unit 12 is alternatively configured to run open-loop and maintain this air purge recirculation state for an amount of time or number of pump strokes that is known or expected, e.g., determined empirically, to satisfactorily drive air back to fluid supply 30. Downstream air detector 72b may again be provided to ensure that air has been removed once air purge valve actuator 16ap is opened to resume pumping and to shut system 310 down if air is detected. Air removal device 60 of system 10 could again be added upstream of air sensor 72a to attempt to eliminate air before triggering the bypass purge sequence.

Fifth Primary Embodiment

Figure 5:
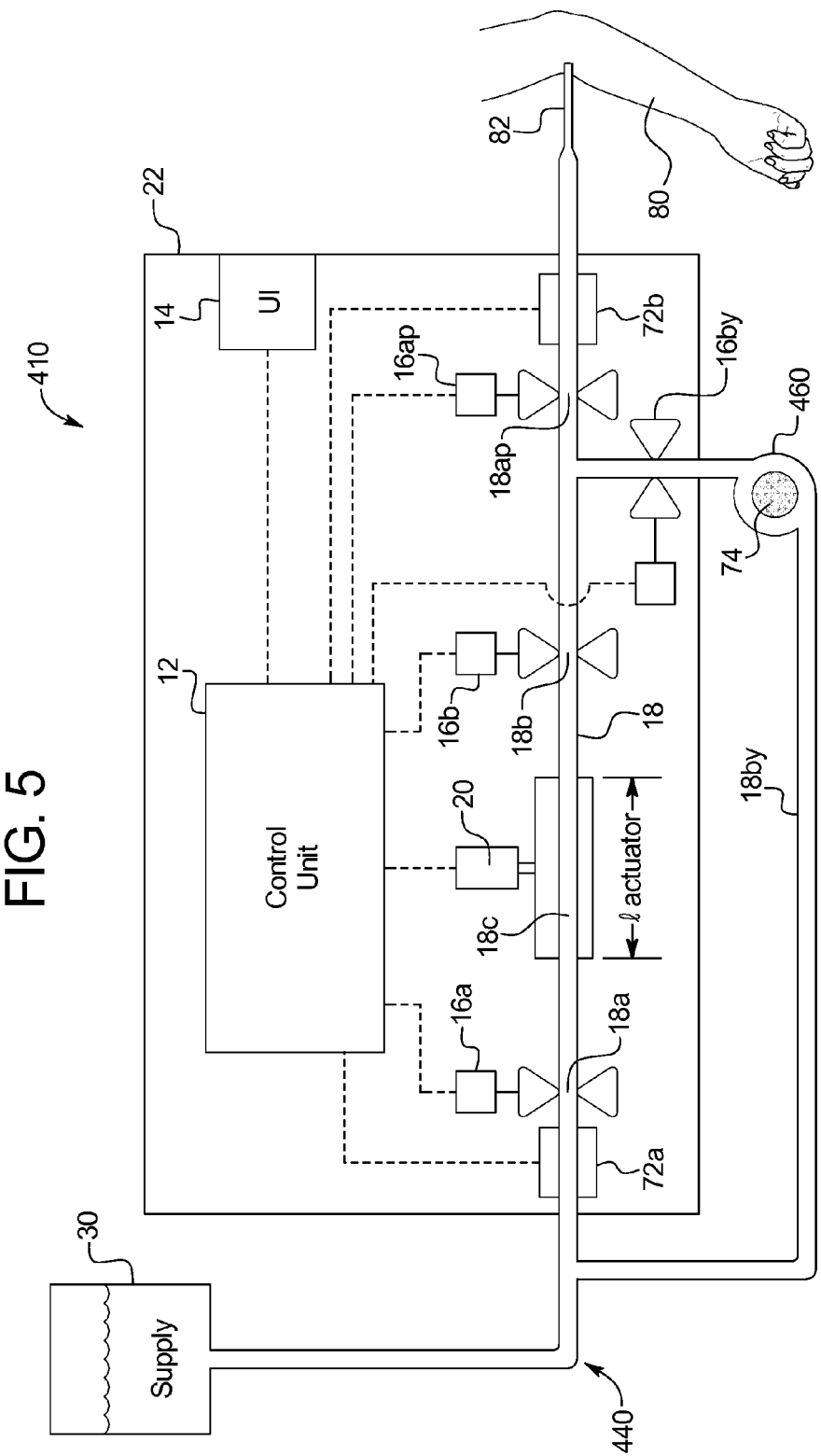
FIG. 5 is a schematic view of a further embodiment of an IV pumping system and method of the present disclosure having a further alternative air removal recirculation bypass and air removal device.

Referring now to FIG. 5, system 410 illustrates another bypass embodiment for an IV pumping system and method having air removal management. System 410 pumps medical liquid in the same way, using the same apparatuses housed in pump housing 22 operating with an IV pump tubing set 440, including all alternatives for those apparatuses discussed herein.

IV pump tubing set 440 includes a bypass line 18by, which returns from a point in the main flow tubing 18 between valve portion 18b and valve portion 18c, not to fluid supply 30 as with system 310, but instead back to main flow tubing 18, upstream of air sensor 72a. Here, bypass line 18by enables air entraining medical fluid to be recirculated past air sensor 72a until it is removed from system 410.

In the illustrated embodiment, a centripetal air/fluid separation device 460 is placed in bypass line 18by. Air separation device 460 is structured to cause an annular or circular liquid path of fluid to flow around hydrophobic or liquid retaining filter 74. Assuming the flowrate of the air-entraining medical liquid to be sufficient, such as 1000 to 4000 milliliters/hour, the heavier liquid tends to be pushed by centripetal force outwardly along an annular, circular or spherical liquid path, causing the air to migrate inwards towards liquid retaining filter 74. Liquid retaining filter 74 is positioned relative to the annular or circular liquid path, so as to make centripetal air/fluid separation device 460 less position or orientation sensitive. Air/fluid separation device 460 can be placed alternatively in main flow tubing 18. Air/fluid separation device 460 removes sensed air from the recirculation bypass loop through main flow line 18 and bypass flow line 18by.

During normal pumping operation, if upstream air sensor 72a detects air in tubing 18, an appropriate signal is sent to control unit 12. Control unit 12, which maintains air purge valve actuator 16ap in an open, e.g., energized state, and bypass valve actuator 16by in a closed, e.g., un-energized, state during normal pumping operation, closes, e.g., un-energizes, air purge valve actuator 16ap and opens, e.g., energizes, bypass valve actuator 16by when air sensor 72a senses air. When air purge valve actuator 16ap is closed and bypass valve actuator 16by is opened, pumping valve actuators 16a and 16b and pump actuator 20 perform at least one pump-out stroke and in an embodiment a series of full pumping strokes. This action circulates air entraining medical fluid through main flow tubing 18 and bypass line 18by to remove air through air removal device 460.

In one embodiment, control unit 12 is configured to monitor air sensor 72a and maintain the bypassing valve and air purge pumping state until air sensor 72a indicates that the main flow medical fluid does not have air. Here, air sensor 72a is again used as a feedback provider to control unit 12. Control unit 12 is alternatively configured to run open-loop and maintain this air purge recirculation state for an amount of time or number of pump strokes that is known or expected, e.g., determined empirically, to satisfactorily drive air out of air/fluid separation device 460. Downstream air detector 72b may again be provided to ensure that air has been removed once air purge valve actuator 16ap is opened to resume pumping and to shut system 410 down if the system senses air. Air removal device 60 of system 10 could again be added upstream of air sensor 72a to attempt to eliminate air before triggering the bypass purge sequence.

For any of the recirculation embodiments of FIGS. 3 to 5, it is contemplated for control unit 12 to be programmed to run the infusion pump actuator 20 and associated valve actuators 16a and 16b as quickly as possible when in the air purge recirculation or bypass mode. By doing so, the time that the drug or medication is not being delivered to the patient is minimized and air is removed as quickly and effectively as possible.

Sixth Primary Embodiment

Figure 6:
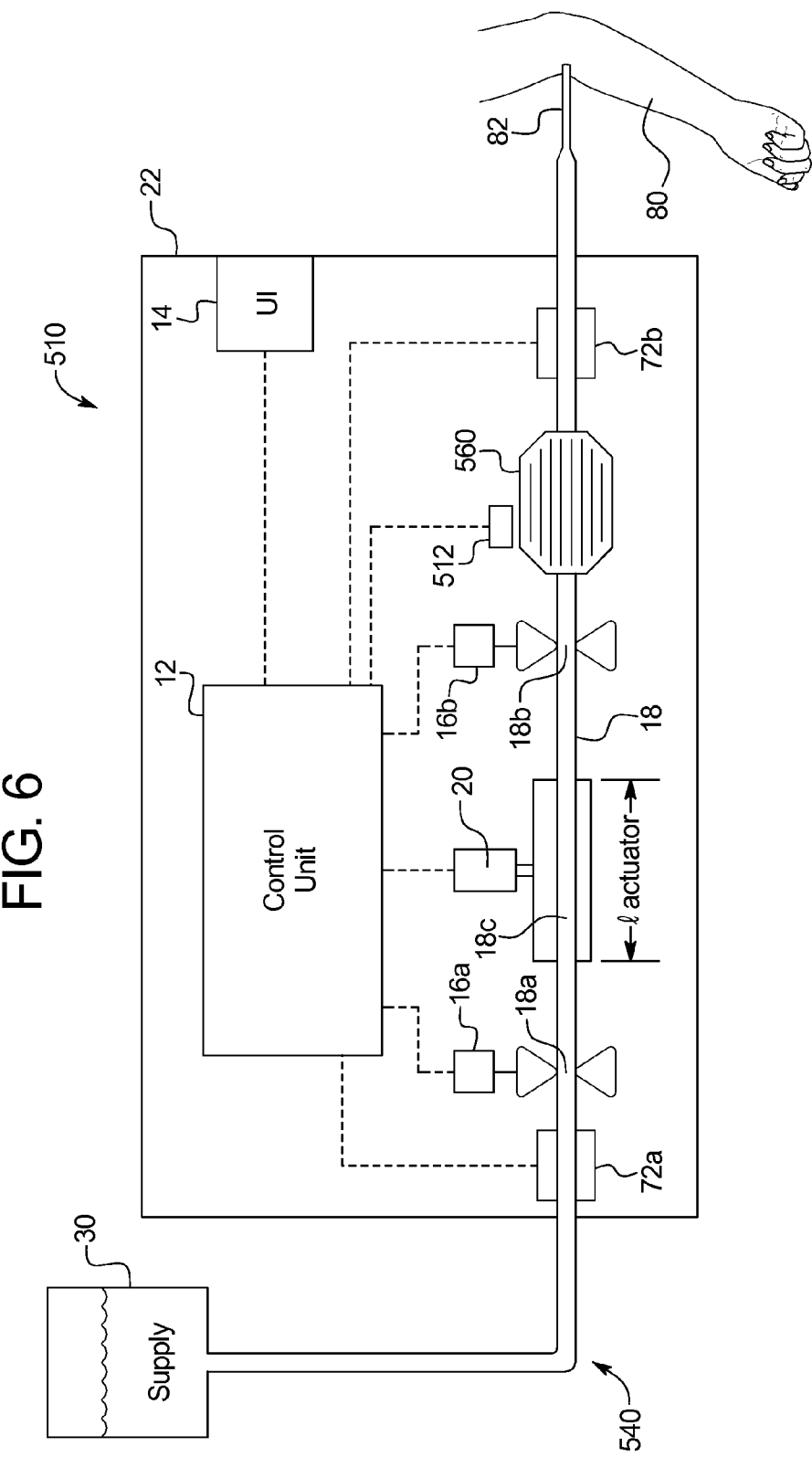
FIG. 6 is a schematic view of one embodiment of an IV pumping system having an inline hydrophobic, air removing dialyzer.

Referring now to FIGS. 6, 7A and 7B, system 510 illustrates another embodiment for an IV pumping system and method having air removal management. System 510 pumps medical liquid in the same way, using the same apparatuses housed in pump housing 22 operating with an IV pump tubing set 540, including all alternatives for those apparatuses discussed herein.

System 510 is similar in some respects to system 110 of FIG. 2. System 510 can provide a sensor 512, which operates with control unit 12 in the same way as does reader 120 of system 110 (which can be used with system 510 instead of sensor 512). Here, sensor 512, a proximity, optical or other sensor, senses the presence of an air removal device 560. If sensor 512 senses air removal device 560, then upstream air detector 72a is used as described below. If sensor 512 does not sense air removal device 560, then upstream air detector 72a is used to shut down system 510 when air detector 72a detects air. Alternatively, sensor 512 is not provided.

Systems 10 and 110 use hydrophobic filters to stop air flow for air removal. Systems 210, 310 and 410 provide a separate air purge valve actuator 16ap to stop main flow through tubing 18, so that air can be purged before being delivered to patient 80. System 510 does not use air purge valve actuator 16ap and relies instead on the path of least resistance through air removal device 550 to effectively urge air out of the device. Downstream air sensor 72b is provided such that if air is able to escape from air removal device 550 in main flow tubing 18, system 510 shuts down pump actuator 20 and closes one or both of valve actuators 16a and 16b. Upstream sensor 72a is used as an early warning air detection device and to allow control unit 12 to integrate the amount of air that passes through tubing 18 during treatment, so that control unit 12 can subtract out the integrated or accumulated air to improve the accuracy of total volume of medical fluid pumped.

FIGS. 7A and 7B illustrate sectioned front elevation and end views, respectively, of air removal device 560, which may be likened to a hydrophobic, air removing dialyzer. Air removal device 560 includes a housing 562, which may be made of any of the medical grade plastic or synthetic materials discussed herein. Housing 562 defines a fluid inlet 564 and a fluid outlet 566. Housing 562 also includes a larger diameter central portion 568. Larger diameter central portion 568 includes or defines one or more air vent 570. Potted ends 572a and 572b are sealed to the inlet and outlet ends of larger diameter central portion 568. Potted ends 572a and 572b are made of a dialyzer potting material, such as polyurethane. Plural hydrophobic hollow fibers 574 extend through and are held sealingly in place by potted ends 572a and 572b.

Hydrophobic hollow fibers 574 are can be made of polyolefins, such as polyethylene or polypropylene. One suitably sized fiber has an average outer diameter of about two-hundred microns and a wall thickness of about thirty microns.

Medical fluid potentially having entrained air enters inlet 564 of housing 562 of air removal device 560. The inlet medical fluid enters an inlet header space 576 before being forced through the inside of one of hollow hydrophobic fibers 574. It is contemplated to provide many hollow fibers 574, such that the cumulative inner diameter area of hollow fibers 574 when compared to the inner diameter area of tubing 18 does not create an undue pressure drop across air removal device 560. Air is removed through air vent 570 from the medical fluid while flow through fibers 574 along larger diameter central portion 568. Purged medical fluid then leaves hollow fibers 574 and gathers in an outlet header space 578 before leaving air removal device 560 through outlet 566. The purged medical fluid is then allowed to flow to patient 80.

One primary vehicle forcing air to leave hollow hydrophobic fibers 574 is least resistance or opportunity. That is, the length of hollow hydrophobic fibers 574 is so much greater than the inner diameter of the fibers that the path of least resistance for an air bubble is to travel radially out of the of hollow hydrophobic fiber 574 as opposed to traveling all the way longitudinally through the fiber. Another way of looking at the mechanism or vehicle is that hollow hydrophobic fibers 574 provide air bubbles with so many opportunities, in close proximity to the fiber walls, to leave hydrophobic fibers 574, that it becomes highly unlikely that any given air bubble will not take one of the opportunities to leave the fiber radially and instead flow al the way through the length of the fiber.

Another primary vehicle forcing air to leave hydrophobic fibers 574 is positive transmembrane pressure. Purged air leaves housing 562 through one or more vent 570. Although air pressure may build outside of hollow hydrophobic fibers 574 and within housing 562, a positive transmembrane pressure gradient will still exist within the device, tending to push the lighter air within the medical fluid towards the inner walls of fibers 574. It is accordingly believed that air removal device 560 may be effective enough so as not to require a hydrophilic filter for blocking air, or a downstream air purge valve for stopping temporarily the flow of medical fluid, as has been described with various ones of the above systems. Also, the positive pressure placement of device 560 within system 510 should preclude the need for a check valve. Further, it is contemplated, as before, to combine features of the other systems if desired, such as a system 10 air removal device 60 upstream of air detector 72.

It should be appreciated that all systems 10, 110, 210, 310, 410 and 510 remove air from tubing 18 and IV pump tubing set 240 without prolonged (or any) interruption of the pumping of the drug, medicament or medical liquid to patient 80. Systems 10, 110 and 510 are in essence blind to the pumping and vice-versa. Systems 210, 310 and 410 stop pumping the medical liquid, medicament or drug momentarily, and without interrupting the operation of valve actuators 16a and 16b and pump actuator 20, to purge air but do not send the system into an alarm state or require a prolonged stoppage of drug delivery.

All systems 10, 110, 210, 310, 410 and 510 are provided with an upstream air detector 72 (system 10) or 72a (remaining systems) placed upstream of the pump actuation area of the pump tubing set to detect air prior to the air reaching the pump. The upstream air sensor 72 and 72a may additionally be used with control unit 12 to integrate the sensed air over time, so that the accumulated air can be subtracted from an assumed amount of total fluid pumped. With shuttle type pump actuator 20, volume of fluid pumped by counting pump strokes of known volumes, the volumes known via known $l_{actuator}$ and the known internal diameter of pump tubing section 18c. It is contemplated to use an air detector that can estimate the size of the air bubbles so that the air volume can be accumulated. It is also contemplated to use multiple air detectors, e.g., spaced ninety degrees from each other to detect each of a pair of air bubbles traveling together.

Systems 110, 210, 310, 410 and 510 also include a second, downstream air detector 72b provided to ensure that the associated system and method has removed the air detected by the upstream air sensor. System 10 can also have such downstream detector 72b. It is contemplated to configure control unit 12, such that the pump actuator 20 and associated valve actuators 16a and 16b are allowed to continue to pump the drug or medication to the patient until the air detected by downstream sensor 72b is calculated to be close to the infusion site. The program or algorithm saved in control unit 12 can take into account a known flowrate, tubing diameter, tubing length and location of the activated air detector 72b relative to the infusion site. Such structure and methodology again maximizes the time that the drug is delivered to the patient, while maintaining safety.

ADDITIONAL ASPECTS OF THE PRESENT DISCLOSURE

Aspects of the subject matter described herein may be useful alone or in combination one or more other aspect described herein. Without limiting the foregoing description, in a first aspect of the present disclosure, an intravenous ("IV") liquid delivery system includes an IV pump tubing set; a pump actuator operable with the IV pump tubing set; and an air removal device located upstream of the pump actuator, the air removal device including a liquid inlet, a liquid outlet, an air collection portion, and a liquid collection portion located adjacent to the liquid outlet, and wherein the air collection portion of the air removal device includes an air passing but liquid retaining filter and a check valve in air flow communication with the air passing but liquid retaining filter.

In accordance with a second aspect of the present disclosure, which may be used in combination with the first aspect, the IV pump tubing set includes an upstream valve portion, a downstream valve portion and a pump portion located between the upstream and downstream valve portions, the system further including upstream and downstream valve actuators operable with the pump actuator to move liquid through the IV pump tubing set.

In accordance with a third aspect of the present disclosure, which may be used in combination with the second aspect, the air removal device is located upstream of the upstream valve portion.

In accordance with a fourth aspect of the present disclosure, which may be used in combination with any one or more of the preceding aspects, the filter is a hydrophobic filter.

In accordance with a fifth aspect of the present disclosure, which may be used in combination with any one or more of the preceding aspects, the liquid collection portion includes a liquid passing but air retainer filter.

In accordance with a sixth aspect of the present disclosure, which may be used in combination with any one or more of the preceding aspects, the IV pump tubing set is configured to be mounted such that the air collection portion is located elevationally above the liquid collection portion.

In accordance with a seventh aspect of the present disclosure, which may be used in combination with any one or more of the preceding aspects, the air removal device includes a housing having a larger cross-sectional area than that of a tube of the IV pump tubing set.

In accordance with an eighth aspect of the present disclosure, which may be used in combination with any one or more of the preceding aspects, the air removal device is provided as part of the IV pump tubing set.

In accordance with a ninth aspect of the present disclosure, which may be used in combination with any one or more of the preceding aspects, the IV liquid delivery system includes at least one air detector located downstream of the air removal device.

In accordance with a tenth aspect of the present disclosure, which may be used in combination with any one or more of the preceding aspects, an intravenous ("IV") liquid delivery system includes an IV pump tubing set; a pump actuator operable with the IV pump tubing set; an air removal device located downstream of the pump actuator, the air removal device including an air passing but liquid retaining filter and a liquid passing but air retaining filter; a device that indicates that the air removal device is present; and a control unit operable with the indicting device, the control unit configured so that when the air removal device is indicated as being present, the pump actuator is allowed to operate the IV pump tubing set even if air is detected upstream of the air removal device.

In accordance with an eleventh aspect of the present disclosure, which may be used with any one or more of the preceding aspects in combination with the tenth aspect, the IV liquid delivery system includes an air detector located downstream of the pump actuator, and wherein the control unit is further configured to stop the pump actuator if air is detected at the downstream air detector.

In accordance with a twelfth aspect of the present disclosure, which may be used with any one or more of the preceding aspects in combination with the tenth aspect, the control unit is further configured so that when the air removal device is indicated as not being present, the pump actuator is stopped if air is detected upstream of the air removal device.

In accordance with a thirteenth aspect of the present disclosure, which may be used with any one or more of the preceding aspects in combination with the tenth aspect, the indicting device includes a sensor positioned to sense the presence of the air removal device.

In accordance with a fourteenth aspect of the present disclosure, which may be used with any one or more of the preceding aspects in combination with the tenth aspect, the indicting device includes a code provided with one of the IV pump tubing set and the air removal device.

In accordance with a fifteenth aspect of the present disclosure, which may be used in combination with any one or more of the preceding aspects, an intravenous ("IV") liquid delivery system includes an IV pump tubing set; a pump actuator operable with the IV pump tubing set; an upstream valve actuator operable with the IV pump tubing set upstream of the pump actuator; a downstream valve actuator operable with the IV pump tubing set downstream of the pump actuator; an air purge valve actuator operable with the IV pump tubing set downstream of the downstream valve actuator; and an air removal device located between the downstream valve actuator and the air purge valve actuator, the system configured to close the air purge valve actuator to force air in the IV pump tubing set to be purged through the air removal device.

In accordance with a sixteenth aspect of the present disclosure, which may be used with any one or more of the preceding aspects in combination with the fifteenth aspect, the pump actuator is a shuttle pump actuator, the shuttle pump or membrane pump actuator operable with the upstream and downstream valve actuators to move liquid through the IV pump tubing set.

In accordance with a seventeenth aspect of the present disclosure, which may be used with any one or more of the preceding aspects in combination with the fifteenth aspect, the air removal device includes an air passing but liquid retaining filter.

In accordance with an eighteenth aspect of the present disclosure, which may be used with any one or more of the preceding aspects in combination with the fifteenth aspect, the IV liquid delivery system is configured and arranged to close the air purge valve actuator for a time or a number of pump-out strokes sufficient to force air in the IV pump tubing set to be purged through the air removal device.

In accordance with a nineteenth aspect of the present disclosure, which may be used with any one or more of the preceding aspects in combination with the fifteenth aspect, the IV pump tubing set includes the air removal device positioned between a downstream valve actuator portion of the IV pump tubing set and an air purge valve actuator portion of the IV pump tubing set.

In accordance with a twentieth aspect of the present disclosure, which may be used with any one or more of the preceding aspects in combination with the fifteenth aspect, the IV liquid delivery system is configured and arranged to maintain open the air purge valve actuator and sequence the pump, upstream and downstream valve actuators for pumping.

In accordance with a twenty-first aspect of the present disclosure, which may be used with any one or more of the preceding aspects in combination with the fifteenth aspect, the IV liquid delivery system includes at least one air detector located upstream or downstream of the pump actuator.

In accordance with a twenty-second aspect of the present disclosure, which may be used with any one or more of the preceding aspects in combination with the fifteenth aspect, the air removal device extends off of a primary liquid delivery line of the IV pump tubing set.

In accordance with a twenty-third aspect of the present disclosure, which may be used in combination with any one or more of the preceding aspects, an intravenous ("IV") liquid delivery system includes an IV pump tubing set; a pump actuator operable with the IV pump tubing set; an upstream valve actuator operable with the IV pump tubing set upstream of the pump actuator; an air detector located upstream of the upstream valve actuator; a downstream valve actuator operable with the IV pump tubing set downstream of the pump actuator; and an air purge valve actuator operable with the IV pump tubing set downstream of the downstream valve actuator, wherein the IV pump tubing set further includes a bypass recirculation line extending from a point located between the downstream valve actuator and the air purge valve actuator to a point in the IV pump tubing set upstream of the air detector, and wherein upon a detection of air in a medical fluid by the air detector, the air purge valve actuator is closed and the pump actuator, the upstream valve actuator and the downstream valve actuator are operated to recirculate the medical fluid using the bypass recirculation line to purge air from the medical fluid.

In accordance with a twenty-fourth aspect of the present disclosure, which may be used with any one or more of the preceding aspects in combination with the twenty-third aspect, the bypass recirculation line extends to a supply of the medical fluid for the IV pump tubing set.

In accordance with a twenty-fifth aspect of the present disclosure, which may be used with any one or more of the preceding aspects in combination with the twenty-third aspect, the bypass recirculation line is in fluid communication with an air removal device to purge air from the medical fluid.

In accordance with a twenty-sixth aspect of the present disclosure, which may be used in combination with any one or more of the preceding aspects, an intravenous ("IV") liquid delivery system includes an IV pump tubing set; a pump actuator operable with the IV pump tubing set; and an air removal device located downstream of the pump actuator, the air removal device including (i) a housing having an inlet end and an outlet end, (ii) a first potted member located adjacent the inlet end, (iii) a second potted member located adjacent the outlet end, and (iv) a plurality of air passing but liquid retaining hollow fibers extending from the first potted member to the second potted member, wherein medical fluid potentially entraining air is passed through the hollow fibers so as to provide a path of least resistance radially out of the hollow fibers.

In accordance with a twenty-seventh aspect of the present disclosure, which may be used with any one or more of the preceding aspects in combination with the twenty-sixth aspect, the IV liquid delivery system includes an air detector located upstream of the pump actuator, the air detector used for at least one of (a) providing an air sense alert and (b) providing a signal used to integrate air volume through the IV pump tubing set.

In accordance with a twenty-eighth aspect of the present disclosure, which may be used with any one or more of the preceding aspects in combination with the twenty-sixth aspect, the IV liquid delivery system includes an air detector located downstream of the air removal device, the air detector used to shut down the system in case air in the IV pump tubing set escapes the air removal device.

In accordance with a twenty-ninth aspect of the present disclosure, which may be used with any one or more of the preceding aspects, an intravenous ("IV") liquid delivery system includes an IV pump tubing set; a shuttle pump or membrane pump actuator operable with the IV pump tubing set; an upstream valve actuator operable with the IV pump tubing set; a downstream valve actuator operable with the IV pump tubing set; the IV pump tubing set including an air removal device; an air detector configured to sense air in the IV pump tubing set; a control unit configured and arranged to (i) open the upstream valve actuator and close the downstream valve actuator to allow the pump actuator to draw liquid into a pump actuation portion of the IV pump tubing set, and (ii) close the upstream valve actuator and open the downstream valve actuator to allow the pump actuator to push liquid out of the pump actuation portion; and wherein the system is configured to attempt to remove the air via the air removal device while operating the upstream and downstream valve actuators according to (i) and (ii).

In accordance with a thirtieth aspect of the present disclosure, which may be used with any one or more of the preceding aspects in combination with the twenty-ninth aspect, the air removal device is located (a) upstream of the upstream valve actuator or (b) downstream of the pump actuator.

In accordance with a thirty-first aspect of the present disclosure, which may be used with any one or more of the preceding aspects in combination with the twenty-ninth aspect, the IV liquid delivery system includes (a) an air detector and (b) an air purge valve actuator located downstream of the downstream valve actuator, the control unit further configured to receive a signal from the air detector indicative of air in the IV pump tubing set and close the air purge valve actuator to attempt to remove the air via the air removal device while operating the upstream and downstream valve actuators according to (i) and (ii).

In accordance with a thirty-second aspect of the present disclosure, any of the structure and functionality illustrated and described in connection with FIG. 1 may be used in combination with any one or more of the preceding aspects.

In accordance with a thirty-third aspect of the present disclosure, any of the structure and functionality illustrated and described in connection with FIG. 2 may be used in combination with any one or more of the preceding aspects.

In accordance with a thirty-fourth aspect of the present disclosure, any of the structure and functionality illustrated and described in connection with FIG. 3 may be used in combination with any one or more of the preceding aspects.

In accordance with a thirty-fifth aspect of the present disclosure, any of the structure and functionality illustrated and described in connection with FIG. 4 may be used in combination with any one or more of the preceding aspects.

In accordance with a thirty-sixth aspect of the present disclosure, any of the structure and functionality illustrated and described in connection with FIG. 5 may be used in combination with any one or more of the preceding aspects.

In accordance with a thirty-seventh aspect of the present disclosure, any of the structure and functionality illustrated and described in connection with FIG. 6 may be used in combination with any one or more of the preceding aspects.

In accordance with a thirty-eighth aspect of the present disclosure, any of the structure and functionality illustrated and described in connection with FIG. 7A may be used in combination with any one or more of the preceding aspects.

In accordance with a thirty-ninth aspect of the present disclosure, any of the structure and functionality illustrated and described in connection with FIG. 7B may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An intravenous ("IV") liquid delivery system comprising:
   an IV pump tubing set including an upstream valve portion, a downstream valve portion, and a pump portion located between the upstream valve portion and the downstream valve portion;
   a pump actuator operable with the pump portion of the IV pump tubing set;
   an air removal device located upstream of the pump actuator, the air removal device including a liquid inlet, a liquid outlet, an air collection portion, and a liquid collection portion located adjacent to the liquid outlet, and wherein the air collection portion of the air removal device includes an air passing but liquid retaining filter and a check valve in air flow communication with the air passing but liquid retaining filter; and
   an air detector located downstream from the air removal device and upstream of the upstream valve portion.

2. The IV liquid delivery system of claim 1, wherein the filter is a hydrophobic filter.

3. The IV liquid delivery system of claim 1, wherein the liquid collection portion includes a liquid passing but air retainer filter.

4. The IV liquid delivery system of claim 1, wherein the IV pump tubing set is configured to be mounted such that the air collection portion is located elevationally above the liquid collection portion.

5. The IV liquid delivery system of claim 1, wherein the air removal device includes a housing having a larger cross-sectional area than that of a tube of the IV pump tubing set.

6. The IV liquid delivery system of claim 1, wherein the air removal device is provided as part of the IV pump tubing set.

7. The IV liquid delivery system of claim 1, wherein the air detector is a first air detector and which includes a second air detector, the first air detector located downstream of the air removal device, and the second air detector located downstream of the downstream valve portion.

8. The IV liquid delivery system of claim 1, wherein the system further includes upstream and downstream valve actuators operable with the pump actuator to move liquid through the IV pump tubing set.

9. The IV liquid delivery system of claim 1, wherein the air removal device is located upstream of the upstream valve portion.

10. An intravenous ("IV") liquid delivery system comprising:
   a pump actuator; and
   an IV pump tubing set including:
      an upstream valve portion,
      a downstream valve portion,
      a pump portion operable with the pump actuator and located between the upstream valve portion and the downstream valve portion,
      an air removal device located upstream of the pump actuator, the air removal device including a liquid inlet, a liquid outlet, an air collection portion, and a liquid collection portion located adjacent to the liquid outlet, and wherein the air collection portion of the air removal device includes an air passing but liquid retaining filter and a check valve in air flow communication with the air passing but liquid retaining filter, and the liquid collection portion includes a liquid passing but air retaining filter; and
      an air detector located downstream from the air removal device and upstream of the upstream valve portion.

11. An intravenous ("IV") liquid delivery system comprising:
   an IV pump tubing set;
   a pump actuator operable with the IV pump tubing set;
   an upstream valve actuator operable with the IV pump tubing set upstream of the pump actuator;
   an air detector located upstream of the upstream valve actuator;
   a downstream valve actuator operable with the IV pump tubing set downstream of the pump actuator; and
   an air purge valve actuator operable with the IV pump tubing set downstream of the downstream valve actuator,
   wherein the IV pump tubing set further includes a bypass recirculation line extending from a point located between the downstream valve actuator and the air purge valve actuator to a point in the IV pump tubing set upstream of the air detector, and wherein upon a detection of air in a medical fluid by the air detector, the air purge valve actuator is closed and the pump actuator, the upstream valve actuator and the downstream valve actuator are operated to recirculate the medical fluid using the bypass recirculation line to purge air from the medical fluid.

12. The IV liquid delivery system of claim 11, wherein the bypass recirculation line extends to a supply of the medical fluid for the IV pump tubing set.

13. The IV liquid delivery system of claim 11, wherein the bypass recirculation line is in fluid communication with an air removal device to purge air from the medical fluid.

14. An intravenous ("IV") liquid delivery system comprising:
   an IV pump tubing set;
   a shuttle pump or membrane pump actuator operable with the IV pump tubing set;
   an upstream valve actuator operable with the IV pump tubing set;
   a downstream valve actuator operable with the IV pump tubing set;
   the IV pump tubing set including an air removal device;
   an air detector configured to sense air in the IV pump tubing set; the air detector located upstream of the upstream valve actuator;
   a control unit configured and arranged to (i) open the upstream valve actuator and close the downstream valve actuator to allow the pump actuator to draw liquid into a pump actuation portion of the IV pump tubing set, and (ii) close the upstream valve actuator and open the downstream valve actuator to allow the pump actuator to push liquid out of the pump actuation portion; and wherein the IV pump tubing set further includes a bypass recirculation line extending from a point located downstream from the downstream valve actuator to a point in the IV pump tubing set upstream of the air detector; and
   wherein the system is configured to attempt to remove the air via the air removal device while operating the upstream and downstream valve actuators according to (i) and (ii).

15. The IV liquid delivery system of claim 14, wherein the air removal device is located (a) upstream of the upstream valve actuator or (b) downstream of the pump actuator.

16. The IV liquid delivery system of claim 14, which includes an air purge valve actuator located downstream of the downstream valve actuator, the control unit further configured to receive a signal from the air detector indicative of air in the IV pump tubing set and close the air purge valve actuator to attempt to remove the air via the air removal device while operating the upstream and downstream valve actuators according to (i) and (ii).

* * * * *